(12) United States Patent
Marangoni

(10) Patent No.: US 9,168,309 B2
(45) Date of Patent: Oct. 27, 2015

(54) THIXOTROPIC COMPOSITIONS

(75) Inventor: Alejandro Marangoni, Guelph (CA)

(73) Assignee: OMNIS BIOTECHNOLOGY INC., Guelph, Ontario (CA)

(*) Notice: Subject to any disclaimer, the term of this patent is extended or adjusted under 35 U.S.C. 154(b) by 0 days.

(21) Appl. No.: 13/876,689

(22) PCT Filed: Nov. 29, 2011

(86) PCT No.: PCT/CA2011/001314
§ 371 (c)(1),
(2), (4) Date: Mar. 28, 2013

(87) PCT Pub. No.: WO2012/071651
PCT Pub. Date: Jun. 7, 2012

(65) Prior Publication Data
US 2013/0184358 A1 Jul. 18, 2013

Related U.S. Application Data

(60) Provisional application No. 61/418,615, filed on Dec. 1, 2010.

(51) Int. Cl.
| | | |
|---|---|---|
| *A61K 47/44* | (2006.01) | |
| *A23D 9/007* | (2006.01) | |
| *C08J 3/09* | (2006.01) | |
| *C08L 91/00* | (2006.01) | |
| *A61K 8/37* | (2006.01) | |
| *A61K 8/73* | (2006.01) | |
| *A61Q 19/00* | (2006.01) | |
| *A61K 8/86* | (2006.01) | |
| *A61K 8/92* | (2006.01) | |
| *C08K 5/101* | (2006.01) | |
| *C08K 5/103* | (2006.01) | |
| *A61K 9/00* | (2006.01) | |
| *A61K 47/14* | (2006.01) | |
| *A61K 47/38* | (2006.01) | |

(52) U.S. Cl.
CPC ............... *A61K 47/44* (2013.01); *A23D 9/007* (2013.01); *A61K 8/375* (2013.01); *A61K 8/731* (2013.01); *A61K 8/86* (2013.01); *A61K 8/922* (2013.01); *A61Q 19/00* (2013.01); *C08J 3/095* (2013.01); *C08K 5/101* (2013.01); *C08K 5/103* (2013.01); *C08L 91/00* (2013.01); *A61K 9/0014* (2013.01); *A61K 47/14* (2013.01); *A61K 47/38* (2013.01); *A61K 2800/10* (2013.01); *C08J 2301/28* (2013.01)

(58) Field of Classification Search
CPC ....... A61K 47/44; A61K 8/375; A61K 8/731; A61K 8/86; A61K 8/922; C08L 91/00; C08J 3/095; C08K 5/101; C08K 5/103; A23D 9/007
See application file for complete search history.

(56) References Cited

U.S. PATENT DOCUMENTS

| | | | | |
|---|---|---|---|---|
| 2,872,332 | A | * | 2/1959 | Grifo et al. ................ 106/252 |
| 3,914,458 | A | | 10/1975 | Terada et al. |
| 3,966,632 | A | | 6/1976 | Colliopoulos et al. |
| 4,446,165 | A | | 5/1984 | Roberts |
| 4,454,113 | A | | 6/1984 | Hemker |
| 4,825,002 | A | | 4/1989 | Davis |
| 4,863,738 | A | | 9/1989 | Taskovich |
| 4,988,612 | A | * | 1/1991 | LaBelle et al. ............. 430/531 |
| 5,236,630 | A | * | 8/1993 | Arima et al. ............... 252/512 |
| 5,472,728 | A | | 12/1995 | Miller et al. |
| 5,633,226 | A | | 5/1997 | Owen et al. |
| 5,646,109 | A | | 7/1997 | Owen et al. |
| 5,688,761 | A | | 11/1997 | Owen et al. |
| 5,843,407 | A | | 12/1998 | El-Nokaly et al. |
| 5,908,631 | A | | 6/1999 | Arnaud et al. |
| 5,948,825 | A | | 9/1999 | Takahashi et al. |
| 6,156,369 | A | | 12/2000 | Eger et al. |
| 6,187,323 | B1 | | 2/2001 | Aiache et al. |
| 6,368,653 | B1 | | 4/2002 | Heertje et al. |
| 6,569,478 | B1 | | 5/2003 | Leser et al. |
| 6,808,737 | B2 | | 10/2004 | Ullanoormadam |
| 6,831,107 | B2 | | 12/2004 | Dederen et al. |
| 6,902,756 | B2 | | 6/2005 | Vlad |
| 7,351,440 | B2 | | 4/2008 | Perks et al. |
| 7,357,957 | B2 | | 4/2008 | Idziak et al. |
| 7,718,210 | B2 | | 5/2010 | Marangoni et al. |
| 2002/0012739 | A1 | | 1/2002 | Cornelissen et al. |
| 2004/0002438 | A1 | | 1/2004 | Hawkins et al. |
| 2004/0086622 | A1 | | 5/2004 | Pelan et al. |
| 2005/0215689 | A1 | * | 9/2005 | Garbar et al. ............. 524/440 |
| 2006/0177491 | A1 | | 8/2006 | Kim |
| 2006/0192180 | A1 | * | 8/2006 | Ichitani et al. ............ 252/500 |
| 2008/0261796 | A1 | * | 10/2008 | Wu et al. ................... 501/32 |

FOREIGN PATENT DOCUMENTS

| | | |
|---|---|---|
| CA | 2171763 | 11/1994 |
| CA | 2048401 | 7/1996 |
| CA | 2096429 | 4/1999 |
| CA | 2126483 | 4/2005 |
| DE | 3814910 | 11/1989 |
| WO | WO 95/35035 | 12/1995 |
| WO | WO 99/62497 | 12/1999 |
| WO | WO2005/107489 | 11/2005 |
| WO | WO2008081175 | 7/2008 |
| WO | WO2008119169 | 10/2008 |
| WO | WO2010143066 | 12/2010 |
| WO | WO2010143067 | 12/2010 |
| WO | WO2012066277 | 5/2012 |
| WO | WO2012162831 | 12/2012 |

OTHER PUBLICATIONS

Chemwatch, Safflower Seed Oil from Carthamus Tinctorius Seed, MSDS, issued: Nov. 14, 2009, p. 1-7.*

(Continued)

*Primary Examiner* — Johann R Richter
*Assistant Examiner* — Genevieve S Alley

(57) ABSTRACT

Thixotropic compositions and methods to produce thereof comprising ethylcellulose, triacylglycerol oil and non-ionic surfactant are provided. The ethylcellulose concentration is in the range of 1-15% and the surfactant to oil ratio is in the range of 40:60 to 60:40.

20 Claims, 16 Drawing Sheets

(56) References Cited

OTHER PUBLICATIONS

Do, T.A.L et al, "Use of ethylcellulose polymers as stabilizer in fat based food suspensions examined on the example of model reduced-fat chocolate" Reactive and Functional Polymers, vol. 70, published online, Aug. 2010, pp. 856-862.

Gravelle, A.J et al.,"Characterization of the Mechanical Properties of Edible Oil organogels for Application in Food System" Physically Inspired Approaches from the Nanoscale to the Microscale. 4th International Symposium. [Online] Aug. 21-24, 2011, Retrieved from Internet: <http://www.uoguelph.cal foodscience/ content! delivery-functionality-complex -food-systems>.

Wood, et al.,"Mechanical Properties of Edible Oil Organogels for Application in Emulsified Meat Batters"Physically-Inspired Approaches from the Nanoscale to the Microscale. 4th International Symposium. [Online] Aug. 21-24, 2011, Retrieved from Internet: <http://www.uoguelph.ca/ foodscience/content!delivery-functionality-complex-food-systems>.

Martinez et al., Influence of the concentration of a gelling agent and the type of surfactant on the rheological characteristics of oleogels, Original Research Article, II Farmaco 58 (2003) pp. 1289-1294.

Aiache, et al. New gelification method for vegetable oils I: cosmetic application, International Journal of Cosmetic Science, vol. 14, Issue 5, pp. 228-234, Oct. 1992.

Gauthier et al., Novel glyceride gels II. Viscosity characteristics, International Journal of Cosmetic Science vol. 18, Issue 5, pp. 229-235, Oct. 1996.

Lee et al., Transdermal Delivery of Theophylline Using an Ethanol/Panasate 800-Ethylcellulose Gel Preparation, Biological & pharmaceutical bulletin 18(1), 176-180, 1995.

Melzer et al., Ethylcellulose: a new type of emulsion stabilizer, European Journal of Pharmaceutics and Biopharmaceutics, vol. 56, Issue 1, Jul. 2003, pp. 23-27.

Sanchez et al., Development of new green lubricating grease formulations based on cellulosic derivatives and castor oil Green Chem., Nov. 2009, 686-693.

Yang et al., Encapsulating aspirin into a surfactant-free ethyl cellulose microsphere using non-toxic solvents by emulsion solvent-evaporation technique, Journal of Microencapsulation Jan. 2001, vol. 18, No. 2: 223-236.

* cited by examiner

THIXOTROPIC COMPOSITIONS

FIELD OF THE INVENTION

The present invention relates generally to ethylcellulose-containing compositions, and in particular, to thixotropic compositions comprising ethylcellulose.

BACKGROUND OF THE INVENTION

Petroleum jelly or petrolatum is a well-known product that has many utilities, including cosmetic-related utilities. Petroleum jelly is an anhydrous semi-solid mixture of hydrocarbons, generally having carbon numbers greater than 25 and a melting-point usually within a few degrees of 75° C. (167° F.). It is colorless, or of a pale yellow color (when not highly distilled), translucent, and devoid of taste and smell when pure. It does not oxidize on exposure to air and is relatively inert. It is insoluble in water and soluble in several organic solvents. Although this product has been found to have many utilities, if prepared improperly, it has been found to contain toxic compounds, including polycyclic aromatic hydrocarbons (PAHs) linked to cancer. As a result, the European Union has classified petrolatum as a carcinogen and restricts its use in cosmetics. Moreover, petrolatum is not extensively used in cosmetic products due to its "greasy feel" on the skin.

Very few non-hydrocarbon-based gels have also been developed for use in cosmetics. U.S. Pat. No. 6,187,323, for example, describes pharmaceutical and cosmetic compositions comprising a mixture of a gelled oil and an aqueous gel. The oil may be gelled with ethylcellulose by heating to 140° C. to dissolve the ethylcellulose. WO2008/081175 also describes an aqueous composition containing an active agent for cosmetic and pharmaceutical applications. This composition is a homogeneous mixture (not emulsion) of an oil component with an aqueous component. The oil component is gelled with ethylcellulose at 120° C. or 150° C. prior to mixing with the aqueous component. The aqueous component is gelled with a conventional cosmetic gelling agent. Aqueous gels such as these, however, do not provide the properties of the anhydrous semi-solid hydrophobic petroleum jelly.

M. A. Ruiz-Martinez et al. in *Il Farmaco*, 58 (2003) 1289-1294 describe compositions formed by dispersing ethylcellulose with certain polyethylene glycol (PEG)—olivate ester surfactants in olive oil at 100° C. Compositions with varying amounts of ethylcellulose, prepared at different temperatures with different surfactants, were made to find a composition suitable for use in drug delivery. The compositions were determined to be unable to recover structurally following shear stress, i.e., were not thixotropic. More importantly, PEG is a petroleum-based compound, and depending on manufacturing processes, PEGs may be contaminated with measurable amounts of 1,4-dioxane, a possible human carcinogen that doesn't easily degrade. Although 1,4-dioxane can be removed from cosmetics during the manufacturing process by vacuum stripping, there is no easy way for consumers to know whether products containing PEGs have undergone this process. PEGs themselves have also shown some evidence of genotoxicity and, if used on broken skin, can cause irritation and systemic toxicity.

U.S. Pat. No. 5,908,631 describes alcohol-free compositions for topical use in which ethylcellulose is solubilized in a solvent such as a natural oil, a trigyceride, a propylene glycol ester, a neopentyl glycol ester, or a fatty alcohol. Propylene glycol esters are made from propylene and fatty acids. Propylene glycol is produced by hydrochlorination of propylene. Propylene (or Propene) is produced from non-renewable fossil fuels—petroleum, natural gas and, to a much lesser extent, coal. Propene is a byproduct of oil refining and natural gas processing. Ethylene, propene, and other compounds are produced by cracking larger hydrocarbon molecules. Propene is separated by fractional distillation from hydrocarbon mixtures obtained from cracking and other refining processes. Neopentyl glycol (IUPAC name 2,2-dimethyl-1,3-propanediol) is an organic chemical compound. It is used in the synthesis of polyesters, paints, lubricants and plasticizers. Neopentyl glycol is synthesized industrially by the aldol reaction of formaldehyde and isobutyraldehyde. This creates the intermediate hydroxypivaldehyde, which can be converted to neopentyl glycol with either excess formaldehyde or catalytic hydrogenation of the aldehyde group to an alcohol group. Thus, this composition is definitely not hydrocarbon-free.

In view of the foregoing, it would be desirable to develop a novel non-hydrocarbon-based composition having more desirable rheological properties.

SUMMARY OF THE INVENTION

Novel thixotropic compositions have now been developed comprising ethylcellulose.

In a first aspect, the present invention provides a thixotropic composition comprising ethylcellulose in combination with at least one oil and a surfactant.

In another aspect, the present invention provides a method of preparing a thixotropic composition comprising:
a) combining ethylcellulose in an amount ranging from 1-15% by weight with an oil and a surfactant, wherein the weight ratio of surfactant to oil is in the range of about 35:65 to 65:35 oil:surfactant to form a mixture;
b) heating the mixture until the ethylcellulose is solubilized; and
c) allowing the mixture to cool to form a thixotropic composition.

In a further aspect, a thixotropic composition is provided comprising ethylcellulose and an oil component, wherein the oil component comprises triacylglycerol oil and a polar acylglycerol oil.

In another aspect, the present invention provides a method of preparing a thixotropic composition comprising:
a) combining ethylcellulose in an amount ranging from 1-15% by weight with an oil component comprising a triacylglycerol oil and a polar acylglycerol oil in a weight ratio of triacylglycerol oil:polar acylglycerol oil of about 40:60 to 60:40 (w/w) to form a mixture;
b) heating the mixture until the ethylcellulose is solubilized; and
c) allowing the mixture to cool to form a thixotropic composition.

These and other aspects of the invention will become more apparent from the following description in which reference is made to the appended drawings.

DETAILED DESCRIPTION OF THE INVENTION

Figure 1A:
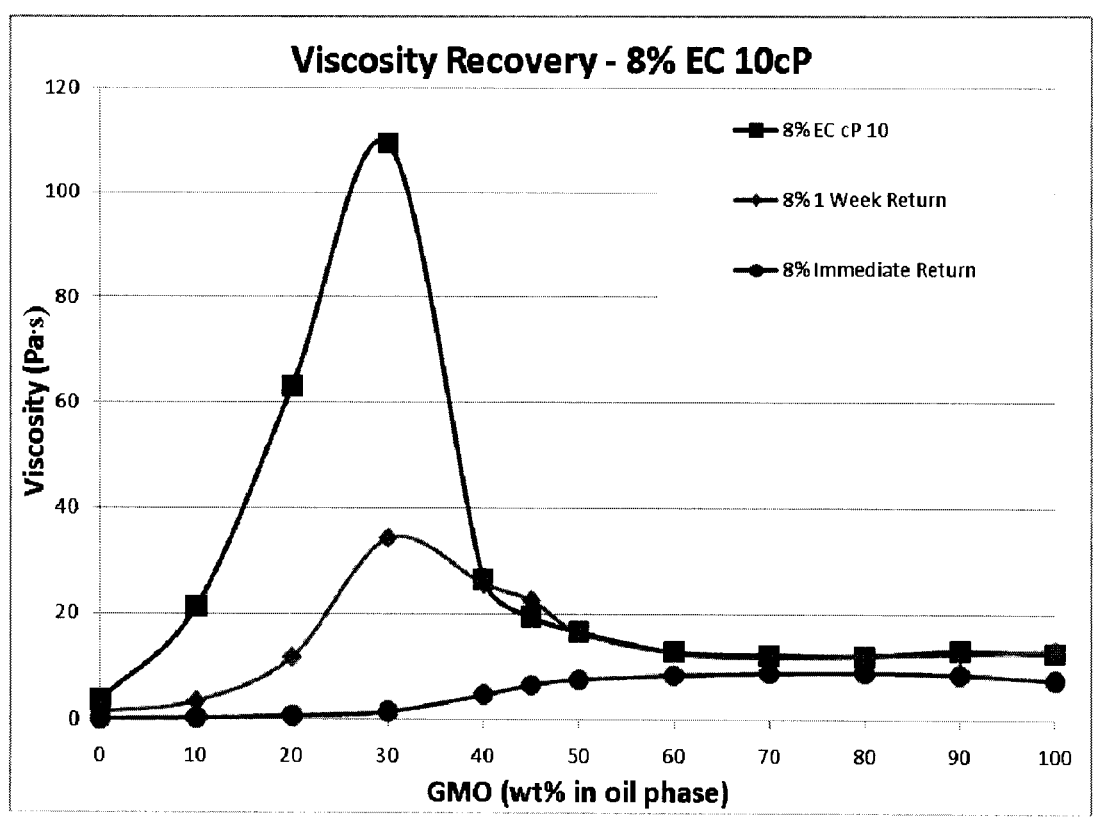
FIG. 1 graphically illustrates the effect of varying the glycerol monooleate (GMO):high oleic sunflower oil (HOSO) weight ratio in compositions comprising 8% ethylcellulose (A) and 5% ethylcellulose (B) on viscosity recovery following shear stress.

In a first aspect, a thixotropic composition comprising ethylcellulose in combination with at least one oil and a surfactant is provided.

The term "thixotropic" as used herein with respect to the present ethylcellulose composition refers to a composition that exhibits a decrease in viscosity from the original equilibrium viscosity when exposed to shear stress, and exhibits viscosity recovery from the decreased post-shear viscosity to the original (e.g. pre-shear) equilibrium viscosity within a finite period of time following cessation of shear stress. In this regard, viscosity recovery refers to at least about 50% recovery to pre-shear equilibrium viscosity, e.g. to at least about 60-80% recovery, preferably to at least about 90%-95% recovery to the original equilibrium viscosity and, more preferably, to recovery of viscosity to essentially the original equilibrium viscosity.

The physical characteristics of the thixotropic composition of the present invention will generally vary with the amounts and nature of each of the components thereof. Thus, the viscosity of the composition decreases with a decrease in the amount of ethylcellulose and a decrease in the molecular weight of ethylcellulose in the composition. The equilibrium viscosity of the composition is preferably less than about 100 Pa s, for example, a viscosity of about 50 Pa s or less, preferably in the range of about 2-30 Pa s, and more preferably in the range of about 10-30 Pa s, such as a viscosity of 20-25 Pa s. As one of skill in the art will appreciate, the target viscosity will vary with the intended utility of the composition. For example, for use in a lip balm, the viscosity may be about 30-40 Pa s, while for use as a moisturizer, the viscosity may be lower than 30 Pa s, such as 15-25 Pa s. Within the foregoing viscosity ranges, the present thixotropic composition will generally be a paste-like composition.

The present composition generally comprises from about 1-15% by weight of ethylcellulose, and preferably from about 5-10% by weight ethylcellulose. As one of skill in the art will appreciate, the molecular weight of the ethylcellulose may vary. The greater the molecular weight, the greater the viscosity of the composition. Generally, ethylcellulose 4 cp, 10 cp, 22 cp, 45 cp, 100 cp, 300 cp and mixtures thereof (cp=centipoise, a measure of the viscosity of a 5% solution of ethylcellulose in a toluene-ethanol solution) may be used in the present compositions to achieve a composition having a target equilibrium viscosity of less than about 100 Pa s. Ethycellulose is a GRAS material (generally regarded as safe) for use in food and cosmetic products, particularly EC 10 cp, EC 22 cp and EC 45 cp. The degree of ethoxylation of ethylcellulose is suitably from about 25% to about 75%, for example from about 40% to about 60%, by weight, which corresponds to a degree of substitution in the range of about 2.3-2.7, and more preferably a degree of substitution of about 2.5.

The oil component of the composition may include one or more of a variety of triacylglycerol oils, including, but not limited to, animal, vegetable, fish, yeast and algal triacylglycerol oils, for example, high oleic acid/low polyunsaturated fatty acid containing oils, for example, vegetable oils, e.g. high-oleic sunflower, high-oleic & high-stearic sunflower oil, high-oleic soybean, high-oleic canola, high-oleic safflower oil, avocado oil and olive oil, and medium and short-chain saturated triglycerides oils such as capryllic-capric triglyceride oils, Neobee oil and coconut oil, soybean oil, canola oil, sunflower oil, safflower oil, corn oil, flaxseed oil, almond oil, peanut oil, pecan oil, cottonseed oil, algal oil, palm oil, palm stearin, palm olein, palm kernel oil, hydrogenated palm kernel oil, hydrogenated palm stearin, fully hydrogenated soybean, canola or cottonseed oils, high stearic sunflower oil, enzymatically and chemically inter-esterified oils, butteroil, cocoa butter, cosmetic oils such as isotridecyl isononanate, and mixtures thereof. Preferably, oils utilized in the present composition do not crystallize extensively (e.g. do not form a strong fat crystal network), are liquid at or above 4° C. and are stable against oxidation, e.g. are not susceptible to oxidation when stored at room temperature for a period of at least about 1 month, and preferably for a period of at least about 3 months or more, e.g. for a period of at least about 6 months. Preferred triglyceride oils include mono, di- or tri-unsaturated oils, preferably mono-unsaturated oils such as oleic acid containing oils, and more preferably, high oleic acid-containing oils, e.g. oils that comprise at least about 50% oleic acid, preferably greater than 60% oleic acid, e.g. at least about 70-80% oleic acid, such as vegetable oils, e.g. high-oleic sunflower, high-oleic & high-stearic sunflower oil, high-oleic soy, high-oleic canola, olive, high-oleic safflower oil, sunflower oil, safflower oil, canola oil, avocado oil, as well a medium and short-chain saturated triglycerides oils such as Neobee oil and coconut oil.

The surfactant component of the composition is a nonionic surfactant, preferably a mono-unsaturated surfactant, and may include mono-unsaturated surfactant selected from the group consisting of a myristoleate, palmitoleate, oleate and gadoleate. Preferred surfactants for use in the present composition are liquid at room temperature, do not crystallize and are transparent. Examples of suitable surfactants include, but are not limited to, polyoxyethylene sorbitan monooleate (Tween 80), sorbitan monooleate (SMO or Span 80), glyceryl monooleate (GMO), glyceryl dioleate (GDO), polyglyceryl ester of oleic acid (PGO), polyglyceryl polyoleate (PGPO), polyglyceryl polyricinoleate (PGPR), triglyceryl monooleate (TGMO) and decaglyceryl decaoleate (DGDO).

The surfactant to oil weight ratio in thixotropic compositions according to the invention may be in the range of about 40:60 to 60:40 (w/w) surfactant:oil, and preferably in the range of about 45:55 to 55:45 (w/w) surfactant:oil. The surfactant:oil component comprises the balance of the composition, e.g. about 85-99% by weight of the composition, depending on the amount of ethylcellulose in the composition.

The present composition is prepared by combining ethylcellulose with an oil and a surfactant to form a mixture, and heating the mixture with constant mixing until the ethylcellulose solubilizes, e.g. to a temperature above the glass transition temperature of the ethylcellulose, e.g. above 130° C., for example, between about 130-160° C., and typically between about 140° to about 150° C. Once the ethylcellulose has fully dissolved and the mixture appears translucent, it is allowed to cool to form a thickened thixotropic composition. Rapid cooling of the mixture, e.g. no more than about 10 minutes after the clear point has been reached, may result in a more homogeneous and stable gel.

In another aspect, a thixotropic composition is provided comprising ethylcellulose and an oil component. The oil component comprises at least one triacylglycerol oil and a polar acylglycerol oil. The ethylcellulose component is as described above. The oil component comprises a triacylglycerol oil to polar acylglycerol oil weight ratio in the range of about 40:60 to 60:40 (w/w) triacylglycerol:polar acylglycerol oil, and preferably in the range of about 45:55 to 55:45 (w/w) triacylglycerol:polar acylglycerol oil. Examples of suitable non polar triacylglycerol oils are set out above. The polar acylglycerol oil is an acylglycerol oil in which the fatty acid component thereof includes polar sidegroups, e.g. hydroxyl groups. Examples of suitable polar acylglycerol oils include castor oil.

The polar acylglycerol oil-containing composition is prepared by combining 1-15% by weight ethylcellulose with the oil component (85-99% by weight) to form a mixture, and heating the mixture with constant mixing until the ethylcellulose solubilizes, e.g. to a temperature above the glass transition temperature of the ethylcellulose, e.g. above 130° C., for example, between about 130-160° C., and typically between about 140° to about 150° C. Once the ethylcellulose has fully dissolved and the mixture appears translucent, it is allowed to cool to form a thickened thixotropic composition.

The present compositions exhibit unique properties including thixotropic properties and vapour barrier properties that render them appropriate for use in cosmetic applications. The compositions, thus, may be used as creams, lotions, balms and the like to function as a skin protectant against drying, chapping, chafing, aging and the like. In this regard, as one of skill in the art will appreciate, the present compositions may be combined with other compositions, such as creams or lotions, including petrolatum or petrolatum-like products. The present compositions may also be combined with components that alter consistency, e.g. with a wax to harden the composition, such as carnauba wax, beeswax, rice bran wax, sunflower wax, candelilla wax, sugarcane wax and the like.

The present thixotropic compositions have been found to function as a vapour barrier. In this regard, the compositions prevent less than about 5% weight loss, e.g. less than about 3%, due to moisture loss in a moisture-containing sample when covered with the composition for a given period of time, e.g. several days such as up to about 5 days.

In addition, the present compositions may be combined with bioactive components, and in particular, lipid-soluble bioactive components to provide the compositions with additional desirable cosmetic or therapeutic properties. Suitable such bioactive components include, but are not be limited to, antioxidants such as alpha-tocopherol, coenzyme-Q, tocotrienols, phytosterols, lycopene, omega-3 fats, essential oils, fragrances and the like.

The present compositions may also be utilized in the food industry for inclusion in foods to maintain a desired level of viscosity in a food such as in spreads, margarines, butters (e.g. peanut and other butters), toppings, fillings, desserts, yoghurts, and the like.

Embodiments of the invention are described by reference to the following specific examples which are not to be construed as limiting.

Example 1

Ethylcellulose Pastes Including Various Oils and Surfactants

Ethylcellulose pastes were made by combining ethylcellulose (EC) 10 cP with an oil, e.g. high oleic sunflower oil (HOSO), high-oleic canola oil (HOCO), Neobee oil, soy oil, canola oil, flax oil and avocado oil, and a surfactant, e.g. glycerol monooleate (GMO), sorbitan monooleate (SMO), polyglyceryl oleate (PGO), sorbitan monostearate (SMS), decaglyceryl decaoleate (DGDO) and triglyceryl monooleate (TGMO) and Tween 80. The mixture was heated with stirring on a hot plate until the ethylcellulose was solubilized. Solubilization was achieved when the solution appeared translucent. The amount of ethylcellulose added was 5-8% by weight. The balance of the composition was oil and surfactant including varying ratios of oil to surfactant from 0:100 to 100:0 (w/w). These samples were tested for viscosity and viscosity recovery (immediate and 1 week after initial testing) and observed for crystallization, separation, flow, stickiness, oiliness, thickness and turbidity, as well as water barrier and binding properties, as detailed below.

Viscosity Measurement

An AR 2000 rheometer (TA Instruments) was used for measuring the viscosity of the gels. The gels were prepared as explained above and left to rest at room temperature (RT≈25° C.) for two days prior to testing. Samples were then pre-sheared by hand using a long, flat, rectangular shaped spatula. Pre-shear was 30 rotations in 30 sec with direction of shear reversed after 15 rotations. The sample was then placed on the Pelletier plate of the rheometer. The geometry used for this analysis was a 60 mm diameter, 2° acrylic cone. The cone was lowered into the sample until a gap size of 900 μm was reached. Any excess sample was removed from the outside of the cone. A stress sweep test was then performed at 25° C. from shear rate of 20-200 s$^{-1}$. A second stress sweep step was performed immediately with shear rate from 200-20 s$^{-1}$. The sample was then removed from the Pelletier plate, placed in a sealed container and stored at room temperature for 1 week. After this period the sample was tested again in the same manner. This procedure was used for all samples unless otherwise indicated.

The viscosity of the samples was interpreted from the results of the above analyses using Rheology Advantage Data Analysis software from TA Instruments. A power law model (Equation 1 below) was fitted to the data from each individual step (from 20-200 s$^{-1}$). The consistency coefficient was chosen to represent the viscosity of the sample.

$$\sigma = k \times \dot{\gamma}^n$$

Where σ is the shear stress, k is the consistency coefficient and $\dot{\gamma}$ is the shear rate.

Physical Characteristics

After testing for viscosity, samples were stored at room temperature and occasionally observed for the following characteristics:

i) Clarity—refers to both the number and size of white crystals as well as any other factor contributing to cloudiness of the sample observed after storage >1 month ii) Separation—any signs of liquid separated from the whole (i.e. liquid observed flowing from the top of the gel-like mass when inverted at an angle iii) Flow—signs of immediate flow of the mass after storage >1 month when observed inverted at an angle. For separated samples, the flow refers to that of the non-separated layer.

Sensory Analysis

The following parameters were used by an individual trained in sensory evaluation of cosmetics to analyse the paste samples:

i) Stickiness—the feeling of stickiness as determined by pressing and releasing middle finger to thumb with sample between ii) Oiliness—feeling of infinite spreadability of sample on skin iii) Thickness—feeling of thickness as determined by shearing the sample on thumb using middle finger in a circular motion Water Vapour Barrier Analysis The method used for analysing the water vapour barrier properties of the samples was similar to that used by Martini et al. 2006, the contents of which are incorporated herein by reference. Paste samples were prepared as above and left at room temperature for 2 days undisturbed. A mixture of 37.5% silica gel, 3% hydroxypropyl methyl cellulose, 13.2% saturated solution of $MgCl_2.6H_2O$, and 46.3% deionized water was prepared. This original mixture was too liquid-like to use for the analysis therefore silica gel was added until a mixture with very little flow was obtained. About 12 g of this mixture was added to plastic AQUALAB cups (Decagon Devices, Inc., WA) and then placed in the freezer (−20° C.) for about 2 hr where it was left to freeze. The paste samples were pre-sheared as in the preparation for viscosity measurements, smeared onto the frozen silica gel cups and evenly smoothed on the top of the cup using a flat spatula. The amount of sample added to the cup was approximately 1.6 g. This process was repeated for petroleum jelly, and oil controls. Cups were also made to represent an uncovered control and completely covered control (with AQUALAB lid in place and parafilm around the seal). Three replicates of each sample were placed on the platform in a sealed dessiccator with a saturated solution of $MgCl_2.6H_2O$ in the bottom of the dessiccator to control the humidity in the dessiccator to 32.9%. The dessiccator was placed in an incubator at 20° C. and the weight change of the samples was measured occasionally. The following equation (2) was used to determine sample weight loss:

$$\% \text{ weight loss} = \frac{w_i - w_t}{w_s} \times 100\%$$

Where $w_i$ is the total initial weight of the sample (including cup, silica, and paste, if present), $w_t$ is the total weight of the sample at time t and $w_s$ is the weight of the silica mixture in the cup.

Water Binding Analysis

Approximately 1 g of product made with 60:40 HOSO:GMO and 8% EC 10 cP was pipetted into the bottom of a tall glass vial. The composition was pre-sheared with a flat spatula by hand with 30 rotations in 30 s. The vial was capped and the samples were left in an incubator at 40° C. for 2 days to encourage any air bubbles to dissipate. After the two days, approximately 1 mL of water or oil was pipetted on top of the composition. Controls were made to account for water or oil that was not absorbed but could not be easily removed from the vial. The controls were made in the same manner as described above, however, the water or oil was poured off and weighed immediately after being added to the composition, i.e. the composition was not allowed to absorb any water or oil. After addition of water or oil, the samples were placed in an incubator at 25° C. for 3 days. The vials were then inverted at an angle for 15 s with shaking to remove the unabsorbed water or oil. The weight of recovered water or oil was weighed and recorded. The amount of absorbed water or oil was calculated by subtracting the wt % recovered at 3 days from the wt % recovered immediately.

Turbidity Analysis

Prepared pastes (60:40 HOSO:GMO and 8% EC 10 cP) were heated up to 60-70° C. to liquefy, poured into 3 mL acrylic cuvettes and allowed to set overnight at room temperature, taking care not to introduce air bubbles in the sample. The turbidity of the gels was then determined by measuring the absorbance of the gel samples in the cuvettes by using a spectrophotometer at a wavelength of 400 nm. A high absorbance (low transmittance, high turbidity), e.g. absorbance of greater than ~0.7, depending on the baseline absorbance of the oil used, is due to the incomplete solubilisation of ethylcellulose in the oil mixture and is indicative of phase separation.

Results

Viscosity Measurement

Figure 1B:
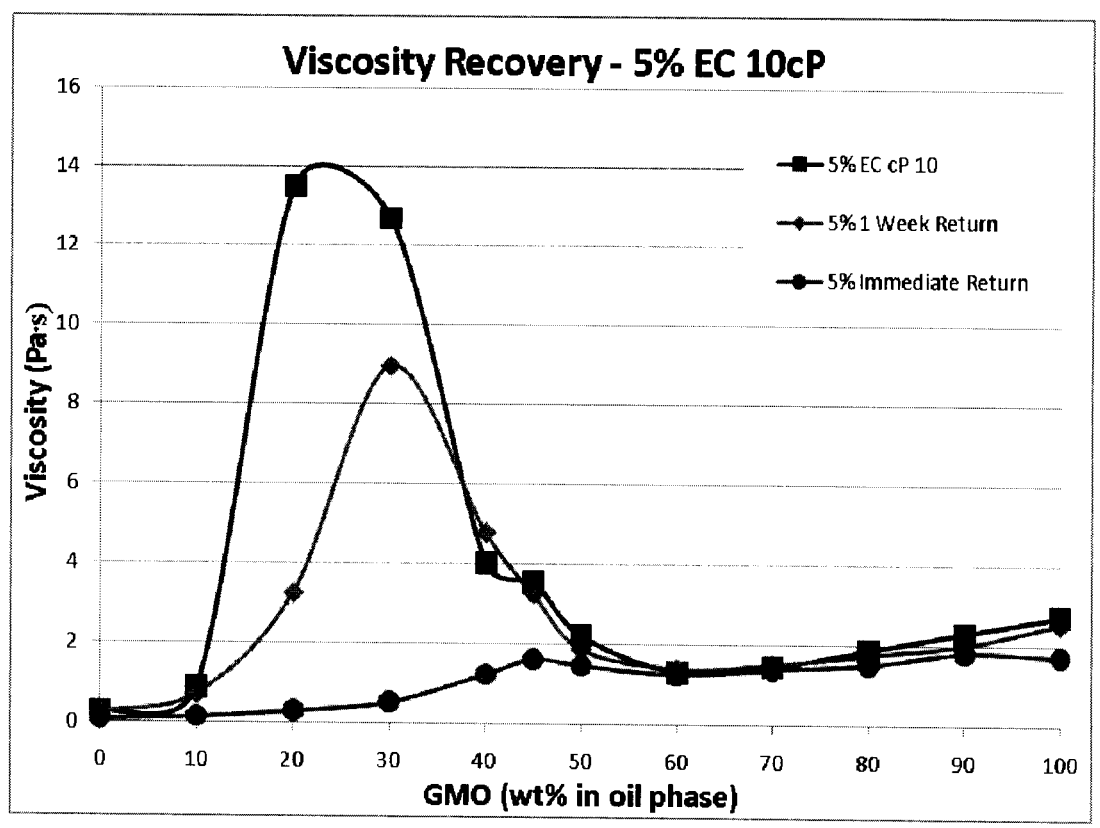

FIG. 1 illustrates viscosity of ethylcellulose pastes having a range of surfactant, e.g. GMO, concentrations. As shown, shearing has the effect of substantially reducing viscosity. This means that the shearing "disrupted" the structure of the pastes, e.g. broke down structure, and the paste appeared more thin or fluid. However, compositions having a GMO concentration of or greater than 40% GMO (of total oil composition) showed recovery of viscosity within 1 week. This means these pastes are time dependent fluids of the thixotropic type—viscosity is lost initially, but then recovers upon standing. Below 40:60 GMO:HOSO, the structure never fully recovers. The mixtures are thus in a gel-state below 40:60 GMO:HOSO and in a reversible, time-dependent state at and above 40:60 GMO:HOSO. The correct terminology would be thixotropic (time-dependent, reversible viscosity loss) at and above 40:60 (GMO:HOSO) and rheodestructive (irreversible viscosity loss) below 40:60 GMO:HOSO. From the data in FIG. 1, a ratio of oil to surfactant in the range of 55:45-45:55 (HOSO:GMO) was preferable. Further experiments were completed using the 55:45 HOSO:GMO ratio only.

Figure 2A:
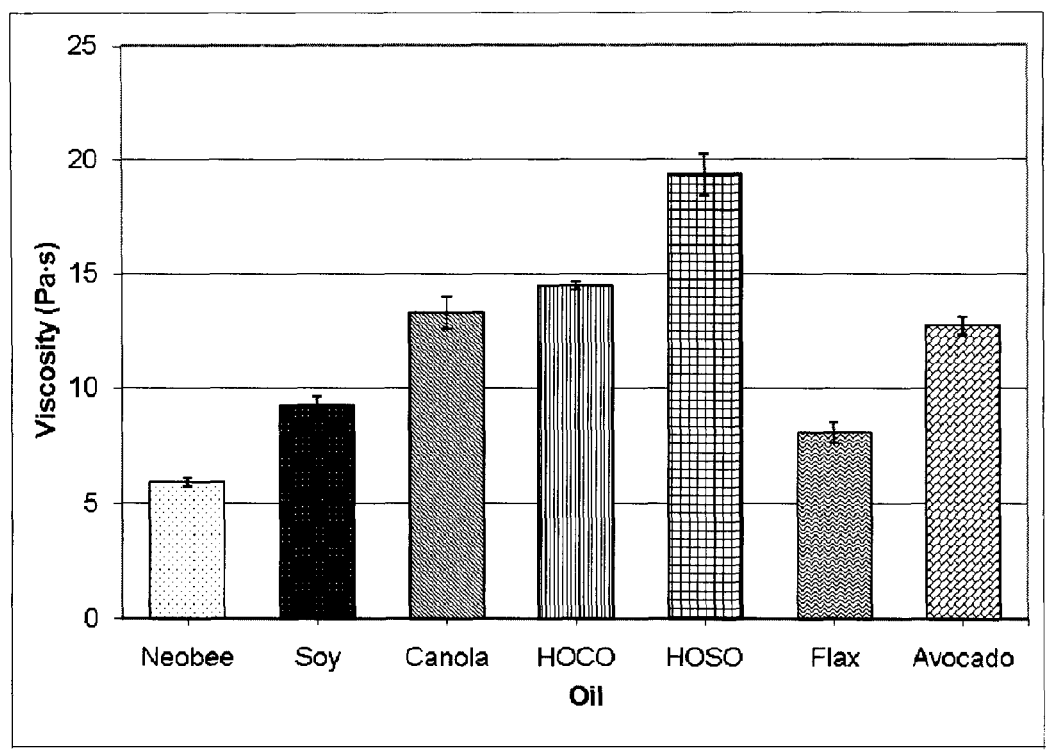
FIG. 2 graphically illustrates the viscosity of ethylcellulose compositions comprising 45:55 (w:w) GMO to various oils (A), and viscosity recovery of such compositions following shearing (B)
Figure 2B:
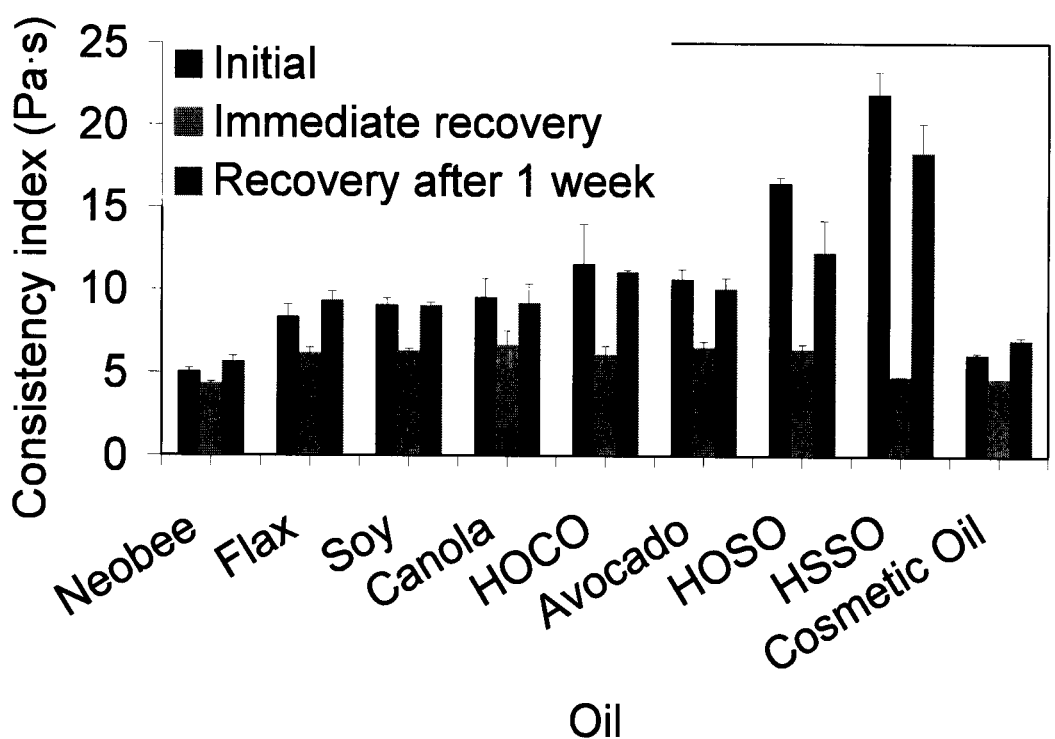

The viscosities of the pastes made with various oils are shown in FIG. 2A. Following shearing as described above, viscosity recovery (e.g. consistency index) was determined after 1 week and is illustrated in FIG. 2B. The results show viscosity recovery in each case, and viscosity recovery of almost 100% in most cases.

Figure 3A:
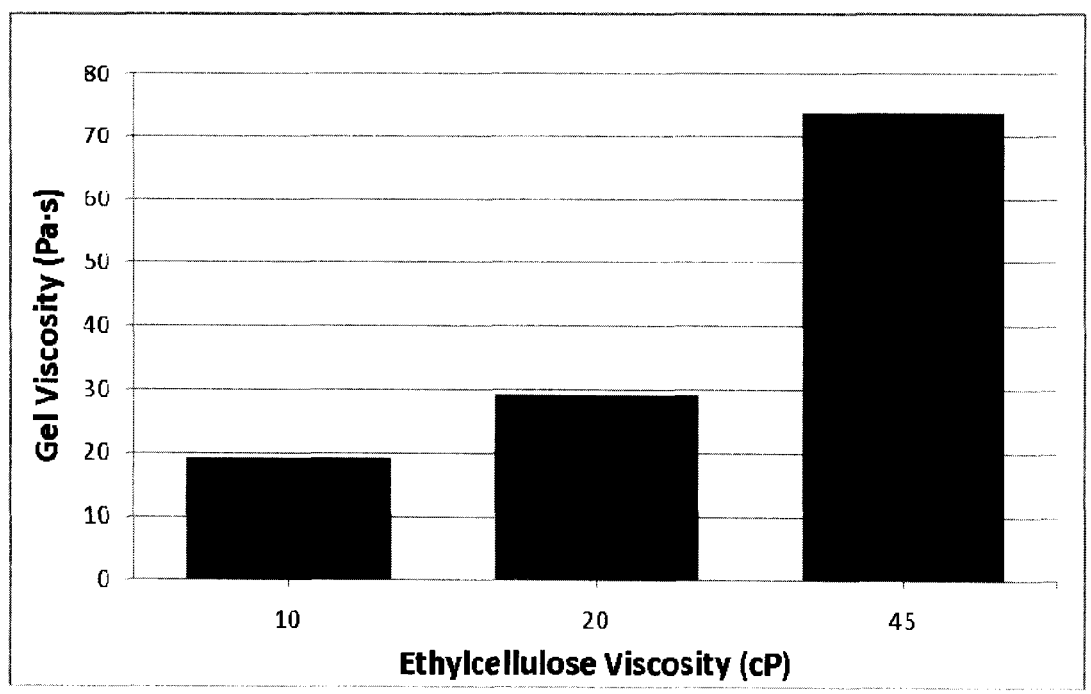
FIG. 3 graphically illustrates the viscosity of compositions comprising 8% ethylcellulose of different molecular weights in 45:55 (w/w) GMO:HOSO (A), and viscosity recovery of such compositions following shearing (B) as well as compositions including mixtures of ethylcellulose of different molecular weights (C)
Figure 3B:
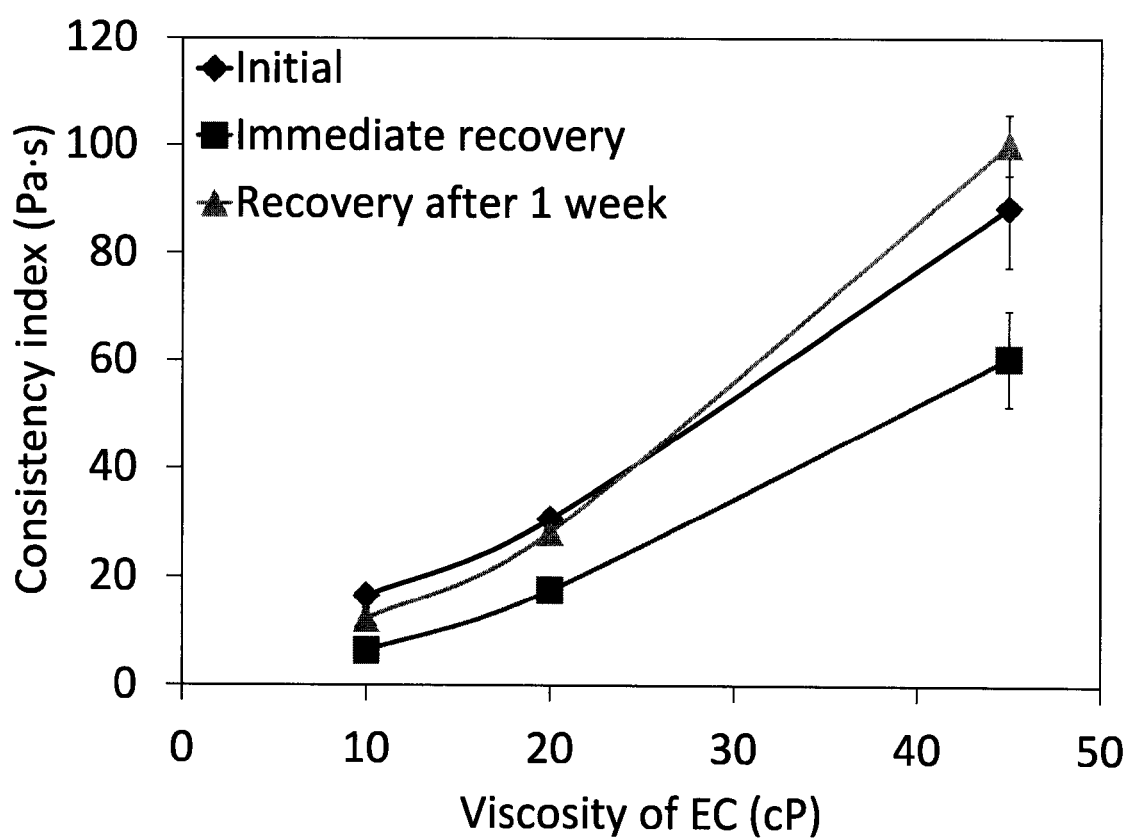
Figure 3C:
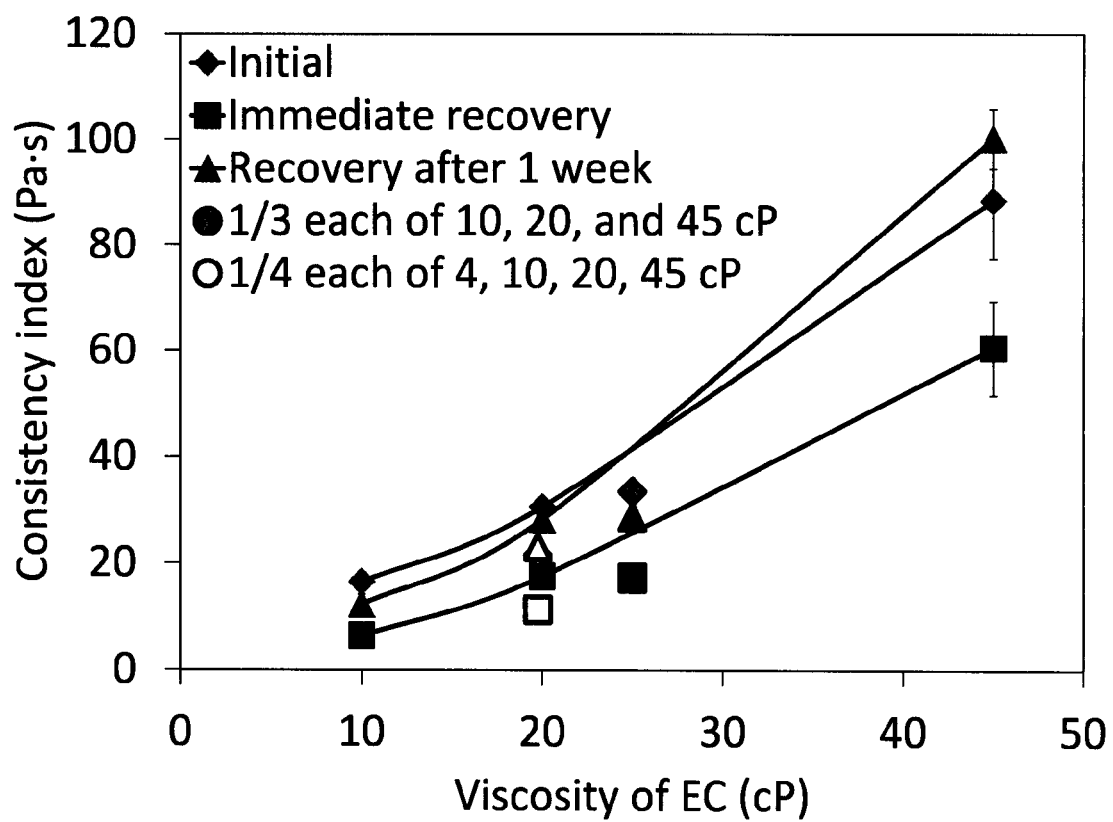

Pastes were also made with 45:55 GMO:HOSO and 8% ethylcellulose (EC) of various viscosities or molecular weights, e.g. 10 cP, 20 cP and 45 cP. The viscosity of the resulting paste was measured. The results are shown in FIG. 3A. The viscosity recovery of these pastes following shearing was also determined as shown in FIG. 3B. Pastes comprising ethylcellulose of varying molecular weight exhibit viscosity recovery. FIG. 3C displays viscosity values for pastes made with mixtures of different EC molecular weights, or viscosities, and the viscosity recovery characteristics of these pastes following shearing. For the gray symbols, 8% EC high-oleic sunflower oils gels (55:45 HOSO:GMO) were prepared using ⅓ of each of 10 cP, 20 cP and 45 cP ethylcellulose. The white symbols correspond to an 8% EC high-oleic sunflower oil gel (55:45 HOSO:GMO) prepared using ¼ of each of 4 cP, 10 cP, 20 cP and 45 cP ethylcellulose. Each of these ethylcellulose combinations also exhibit viscosity recovery. These data demonstrate that a thixotropic paste can be prepared using a single EC molecular weight or a combination of molecular weights. An effective molecular weight can readily be achieved by a simple linear combination of EC of different molecular weights.

Figure 4:
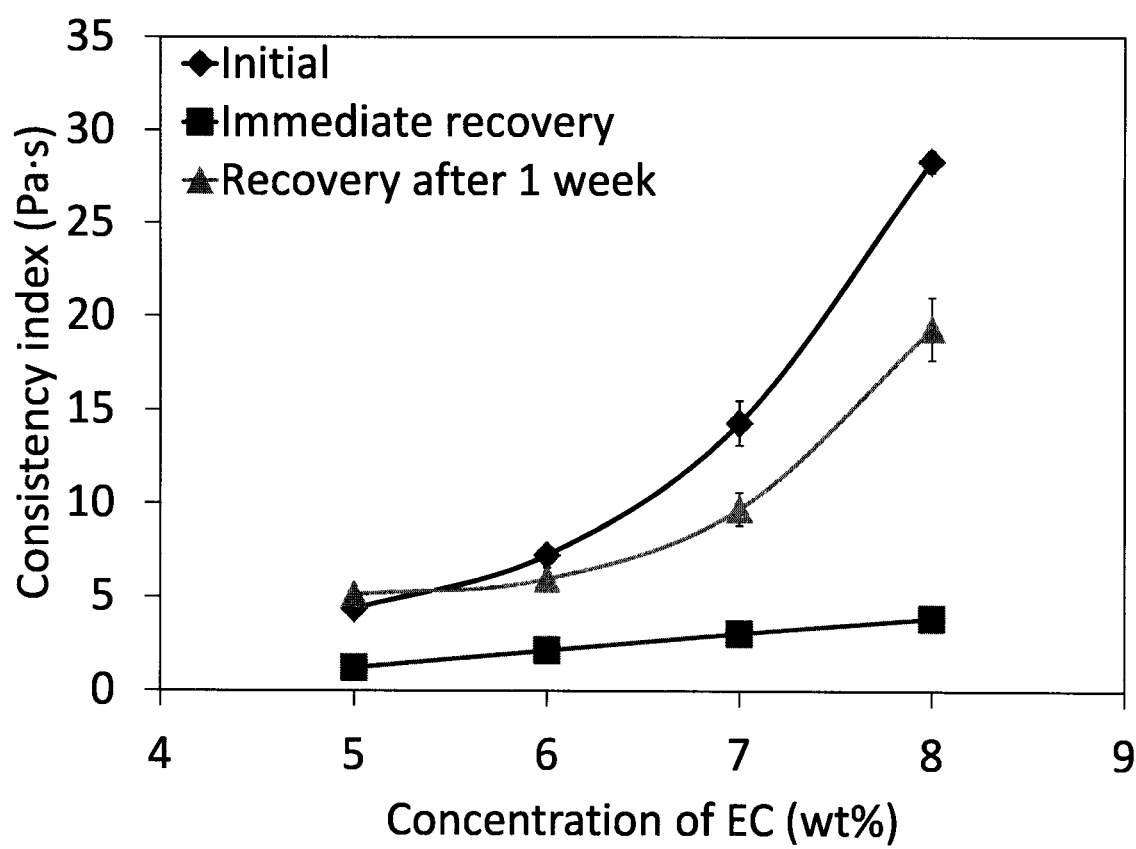
FIG. 4 graphically illustrates the viscosity of compositions comprising varying concentrations of ethylcellulose 10 cP in 45:55 (w/w) GMO:HOSO.

Paste samples were then made with 45:55 GMO:HOSO and various concentrations of EC 10 cP. The results are shown in FIG. 4.

Figure 5A:
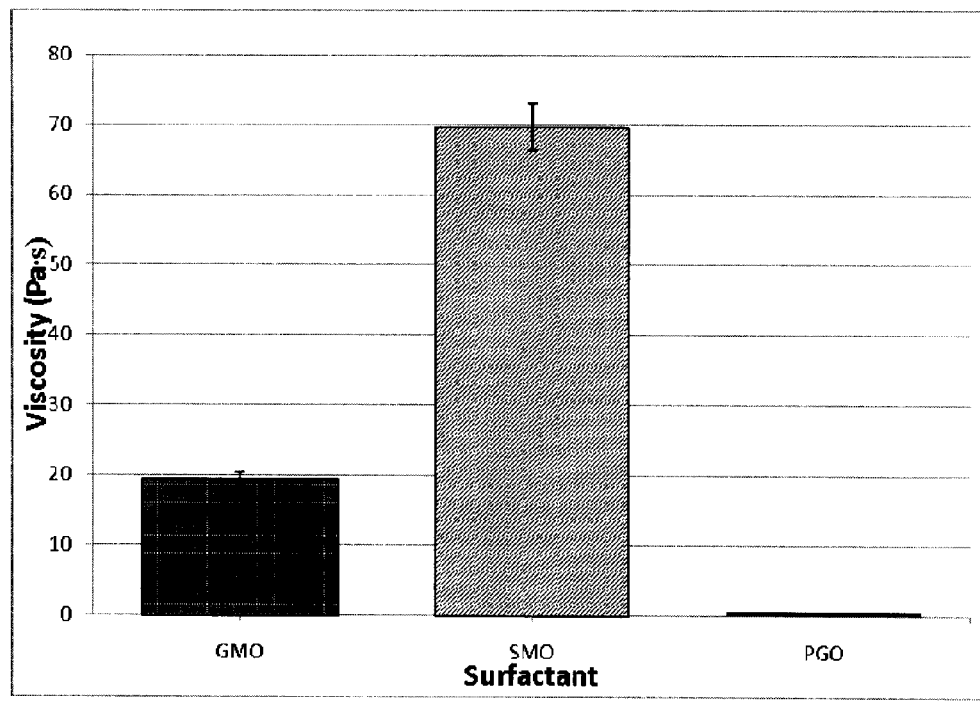
FIG. 5 graphically illustrates the viscosity of 8% ethylcellulose 10 cP compositions comprising HOSO and various surfactants in a 55:45 (w/w) ratio (A), and viscosity recovery of such compositions following shearing (B)
Figure 5B:
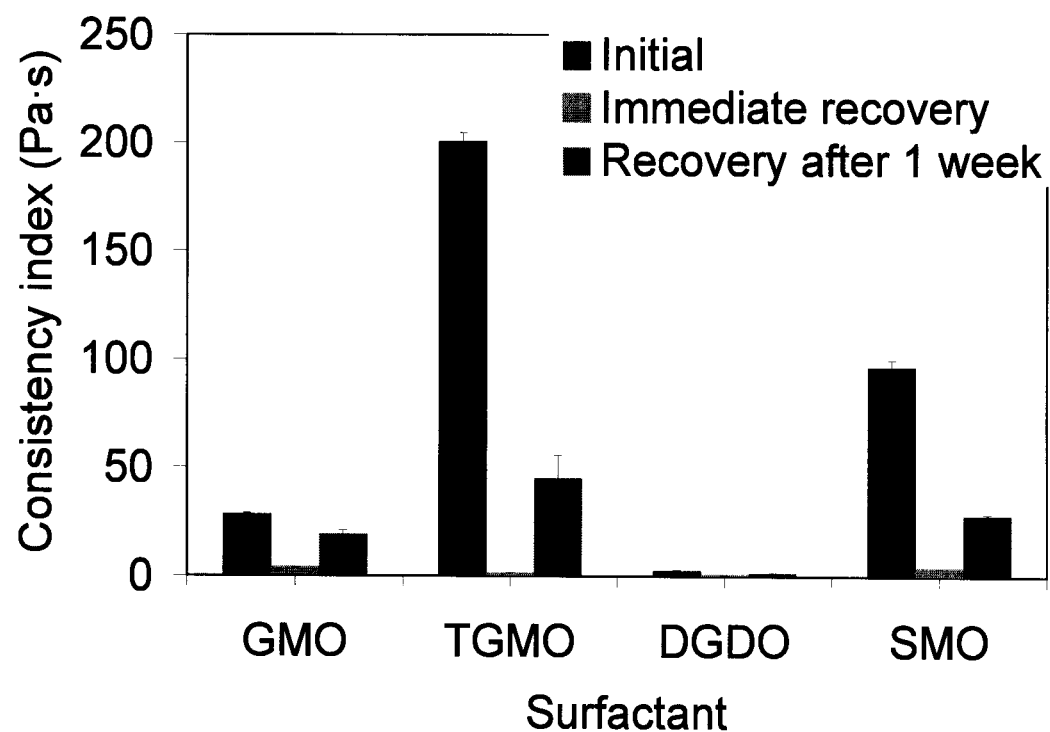

The effect of surfactant type was also studied. Samples were made with a ratio of 45:55 surfactant:HOSO with 8% EC 10 cP. The viscosities of the resulting pastes made with GMO, sorbitan monooleate (SMO), or polyglyceryl oleate (PGO) are shown in FIG. 5A. Following shearing as described above, viscosity recovery (e.g. consistency index) was determined after 1 week and is illustrated in FIG. 5B. The results show significant viscosity recovery in each case.

Samples were also made with sorbitan monostearate (SMS), and Tween 80; however, the viscosity of both of these samples could not be tested using the rheological method described above. The formula which included SMS as the surfactant produced a sample that was solid at room temperature. The sample with Tween 80 was somewhat gel-like but when sheared produced small clumps. These clumps were hard and the oil was squeezed out of them when the rheological test was attempted. The SMO product was orange in colour.

Physical Characteristics

The characteristics of sample products were observed as set out in Table 1 below.

TABLE 1

| Sample Description | | Characteristics | | |
|---|---|---|---|---|
| | Surfactant:Oil | Clarity | Separation | Flow |
| 5% EC 10 cP | 100:0 | Many crystals and cloudy bands | None | Some |
| GMO:HOSO | 90:10 | Many crystals and cloudy | None | Much |
| | 80:20 | Some very small crystals on bottom | None | Much |
| | 70:30 | Few crystals on bottom | None | Much |
| | 60:40 | Few crystals on bottom | None | Much |
| | 50:50 | Clear | None | Much |
| | 45:55 | Clear | None | Some |
| | 40:60 | Clear | None | Little |
| | 30:70 | Cloudy | Much | Some |
| | 20:80 | Cloudy | Much | Some |
| | 10:90 | Cloudy | Much | Some |
| | 0:100 | Bottom cloudy, top clear | Much | Much |
| 8% EC 10 cP | 100:0 | Many crystals and cloudy bands | None | None |
| GMO:HOSO | 90:10 | Many crystals and cloudy | None | Little |
| | 80:20 | Many crystals and cloudy | None | Little |
| | 70:30 | Many crystals | None | Little |
| | 60:40 | Many small crystals | None | Little |
| | 50:50 | Clear; very few crystals | None | Very little |
| | 45:55 | Clear | None | Very little |
| | 40:60 | Clear | None | None |
| | 30:70 | Somewhat cloudy | Much | None |
| | 20:80 | Cloudy with bubbles | Much | Some |
| | 10:90 | Cloudy | Much | Much |
| | 0:100 | Cloudy | Much | Much |
| 8% EC; | EC 10 cP | Clear | None | Very little |
| 45:55 | EC 20 cP | Clear | None | Very little |
| GMO:HOSO | EC 45 cP | Clear | None | Very little |
| EC 10 cP | 5% EC | Clear | None | Little |
| 40:60 | 6% EC | Clear | None | Little |
| GMO:HOSO | 7% EC | Clear | None | Very little |
| | 8% EC | Clear | None | None |
| 8% EC 10 cP | HOSO | Clear | None | Very little |
| 45:55 | Soybean | Clear; slight orange tinge | None | Some |
| GMO:Oil | Canola | Clear; slight yellow tinge | None | Very little |
| | Flax Seed | Some crystals; cloudy; orange | None | Some |
| | Neobee | Clear; colourless | None | Much |
| | HOCO | Clear | None | None |
| | Avocado | Clear; green | None | None |
| 8% EC 10 cP | GMO | Clear | None | Very little |
| 45:55 | SMO | Very cloudy; dark orange | Some | None |
| Surfactant:HOSO | PGO | Clear | None | Much |
| | SMS | Opaque; off-white; solid | None | None |
| | Tween 80 | Cloudy; chunky | Much | Some |
| Vaseline | | Cloudy/opaque; slightly yellow | None | None |

Sensory Analysis

Many of the pastes were analysed for thickness, stickiness, and oiliness as described above. Thickness and stickiness were rated on a scale of 0-5 and oiliness was described as either oily or not oily. The results are set out in Table 2 below.

TABLE 2

| Sample Description | | Surfactant:Oil | Stickiness | Thickness |
|---|---|---|---|---|
| 8% EC 10 cP; GMO:HOSO | | 100:0 | 5 | 5 |
| | | 90:10 | 5 | 4.5 |
| | | 80:20 | 4.5 | 4.5 |
| | | 70:30 | 4.5 | 4.5 |
| | | 60:40 | 3.5 | 2.5-3 |
| | | 50:50 | 4 | 3.5 |
| | | 45:55 | 3 | 3-3.5 |
| | | 40:60 | 2.5-3 | 2.5 |
| | | 30:70 | 2.5 | 2.5 |
| | | 20:80* | 2.0 | 1.5 |
| | | 10:90* | 0 | 0.5 |
| | | 0:100* | 0 | 0 |
| 8% EC; 45:55 GMO:HOSO | | EC 10 cP | 3.5 | 3 |
| | | EC 20 cP | 3.25 | 2.5 |
| | | EC 45 cP | 3.5 | 2.5 |
| EC 10 cP; 40:60 GMO:HOSO | | 5% EC* | 2 | 2 |
| | | 6% EC* | 1.5 | 1 |
| | | 7% EC | 2 | 1.5 |
| | | 8% EC | 2.5-3 | 2.5 |
| 8% EC 10 cP 45:55 GMO:Oil | | HOSO | 3.5 | 3 |
| | | Soybean | 3.5 | 2.5 |
| | | Canola | 2.5 | 2 |
| | | Flax Seed | 2.5 | 2.5 |
| | | Neobee | 2 | 1.5 |
| | | HOCO | 3 | 2.5 |
| | | Avocado | 4 | 3.5 |
| Vaseline | | | 2.5 | 3-3.5 |
| HOSO | | | 0.5 | 1 |
| GMO | | | 1 | 1 |
| GMO:HOSO | | 40:60 | 0.5 | 0.5 |

*Samples felt oily

Water Vapour Barrier Analysis

Figure 6A:
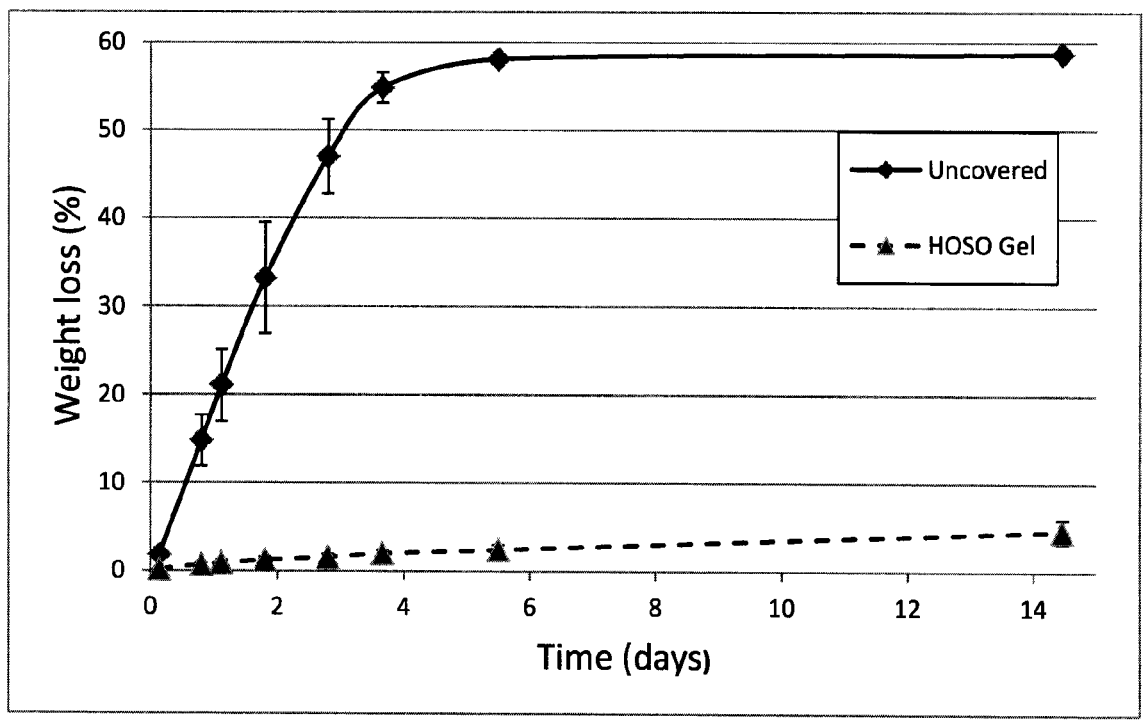
FIG. 6 graphically illustrates the water vapour barrier properties of an 8% ethylcellulose 10 cP composition comprising 45:55 (w/w) GMO:HOSO (A), as well as a comparison of 8% ethylcellulose 10 cP compositions comprising 40:60 (w/w) GMO and different oils (B)
Figure 6B:
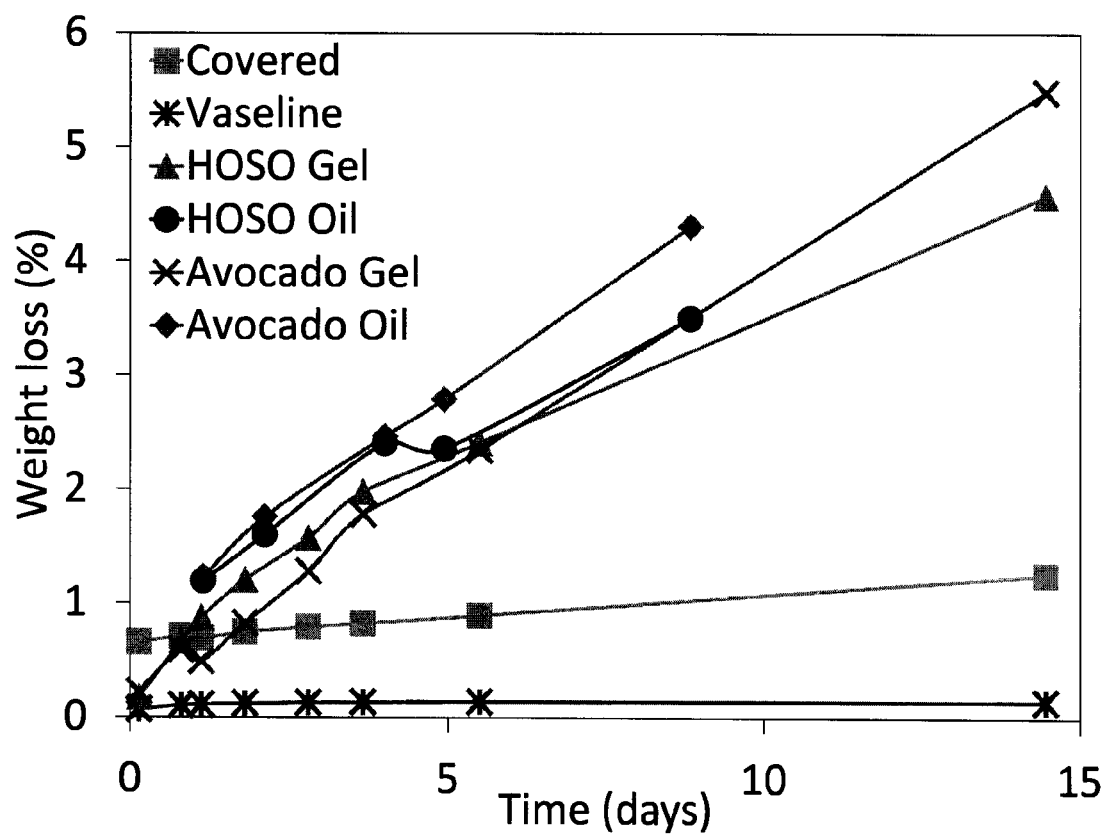

A water vapour barrier test was performed as described above. The samples used included a paste made with 8% EC 10 cP and HOSO (45:55 GMO:HOSO) (FIG. 6A), as well as a paste made with 8% EC 10 cP and either HOSO or avocado oil in a ratio of 40:60 GMO:oil (FIG. 6B). Commercially available Vaseline petroleum jelly was used as a comparison for the above samples. As can be seen in FIG. 6, each of the samples exhibited less than 3% weight loss at up to 5 days of incubation.

Water Binding Analysis

Figure 7:
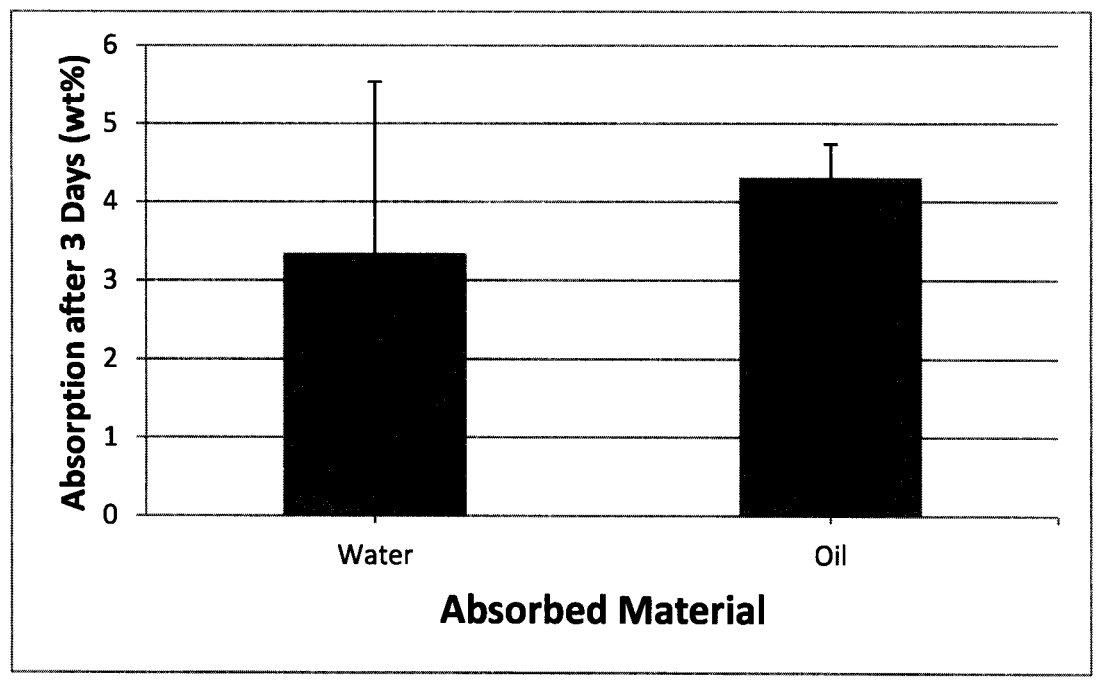
FIG. 7 graphically illustrates oil and water absorption of an 8% ethylcellulose 10 cP composition comprising 45:55 (w:w) GMO:HOSO.

Pastes had the ability to bind water and oil to an extent of 3.3% and 4.3% of the water and oil phase added on top of the paste, respectively, as illustrated in FIG. 7.

Turbidity Analysis

Figure 8A:
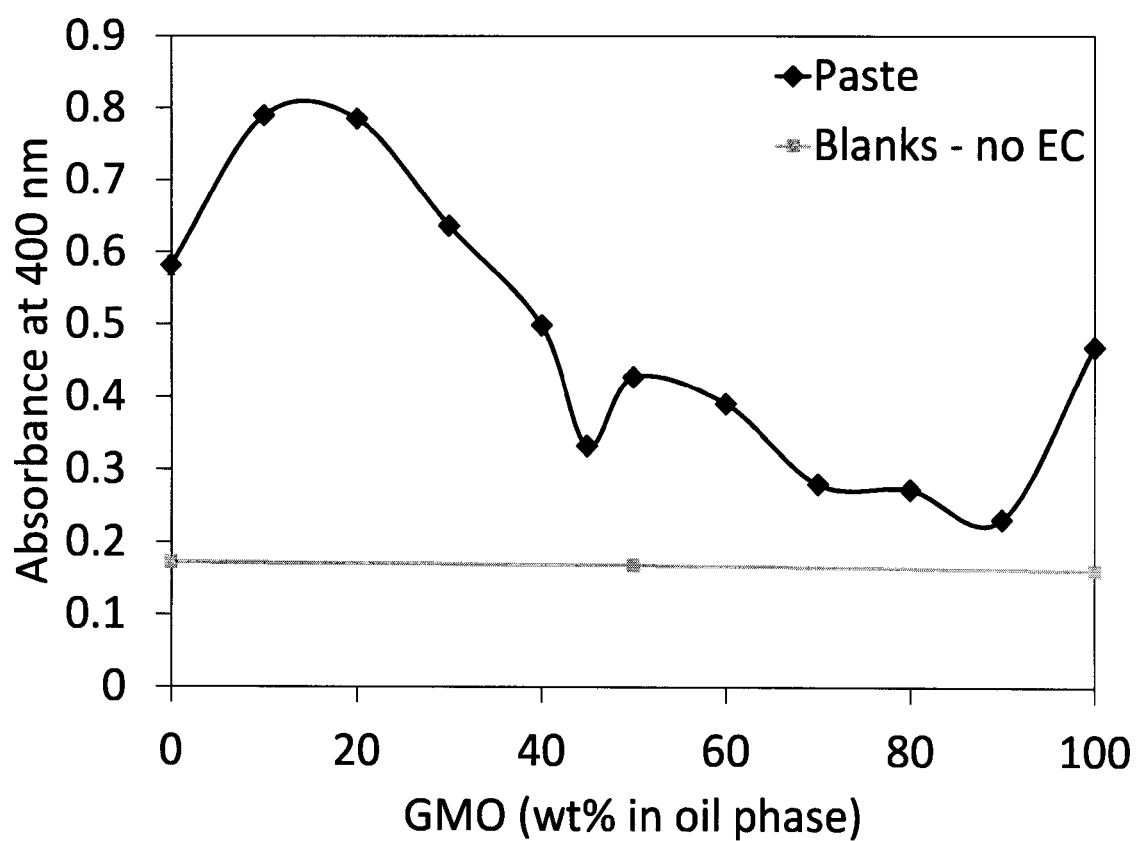
FIG. 8 graphically illustrates the turbidity in terms of absorbance of surfactant-(A) and castor oil-(B) containing thixotropic compositions.

Gels exhibiting an absorbance of greater than about 0.7 were considered to be unstable, with poor clarity and limited stability. FIG. 8A demonstrates that the pastes/gels are quite turbid below 40% (w/w) GMO:oil, and that above 45% GMO:oil (w/w), the sample has a minimal turbidity, and hence is clear and homogeneous. This low turbidity or high transparency correlates with surfactant:oil ratios of compositions which exhibit thixotropic properties indicating that maximal EC solubilisation is achieved in thixotropic compositions.

Example 2

Ethylcellulose Paste with Castor Oil

An ethylcellulose paste (8% EC 10 cP) in HOSO:castor oil was prepared as described in Example 1 with varying amounts of castor oil in HOSO.

Figure 9:
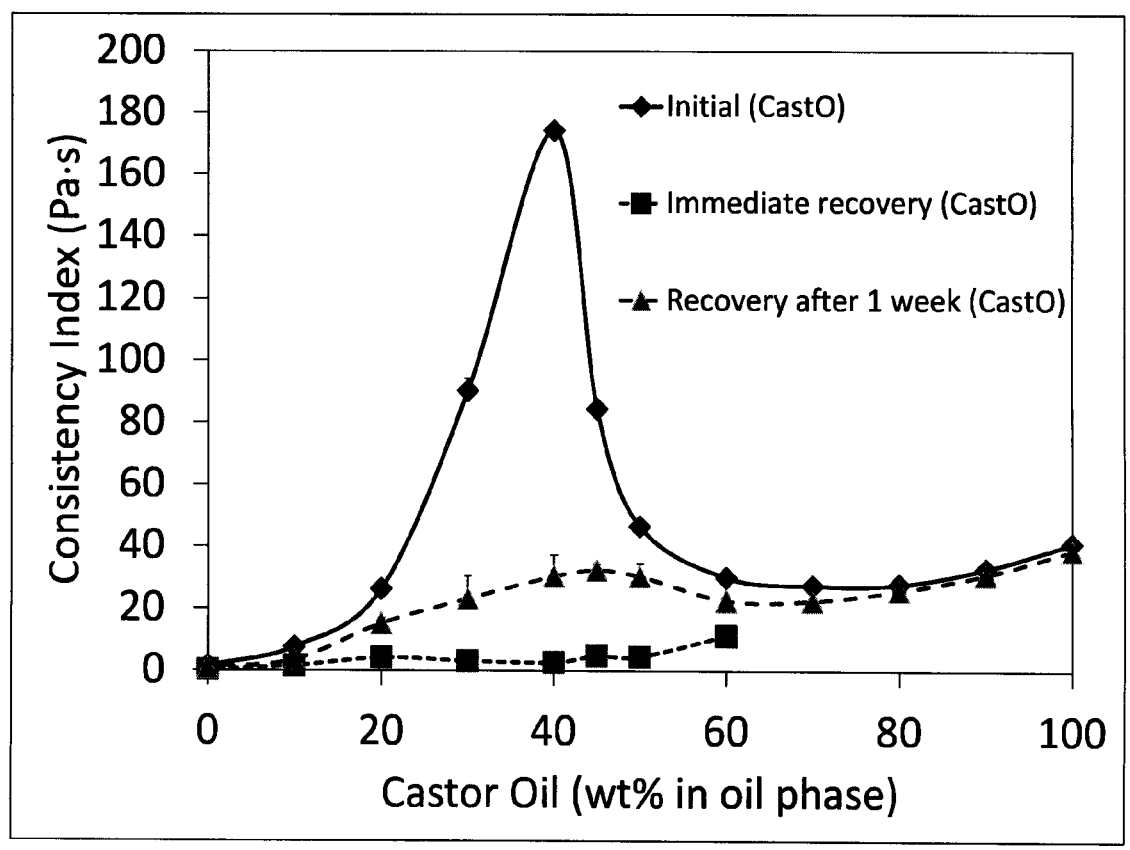
FIG. 9 graphically illustrates viscosity recovery of ethylcellulose compositions containing castor oil following shearing.

The viscosity of each paste made with various amounts of castor oil is shown in FIG. 9. Following shearing as described above, viscosity recovery (e.g. consistency index) was determined after 1 week and is illustrated in FIG. 9. The results show viscosity recovery in compositions comprising a wide range of castor oil concentrations, with viscosity recovery of at least about 50% evident in samples comprising at least about 40% by wt castor oil, preferably at least about 45% by wt castor oil (55% by wt HOSO) up to about 65% by wt castor oil (35% by wt HOSO).

Figure 8B:
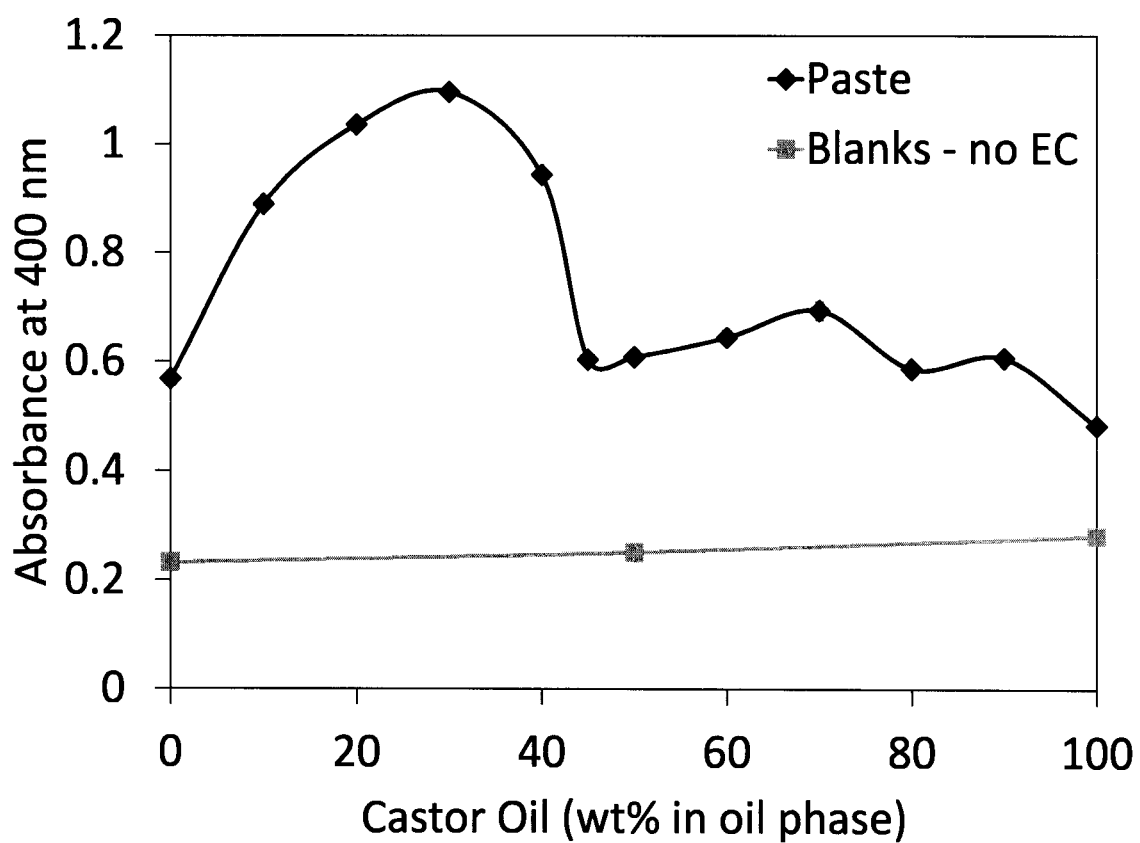

Turbidity analysis of this composition was also determined. FIG. 8B illustrates that minimum turbidity and maximal transparency and stability are observed at castor oil:HOSO ratios at and above 45:55 (w/w).

The above embodiments have been described by way of example only. Many other embodiments falling within the scope of the accompanying claims will be apparent to the skilled reader.

The invention claimed is:

1. A thixotropic composition comprising ethylcellulose in combination with a triacylglycerol oil and a non-ionic surfactant, wherein the ethylcellulose concentration is in the range of about 1-15 wt % and the combination of the triacylglycerol oil and surfactant is in the range of about 85-99 wt %, wherein the surfactant to oil ratio is in the range of about 40:60 to 60:40 (w/w) surfactant to oil.

2. The composition of claim 1, wherein the surfactant to oil ratio is in the range of about 45:55 to 55:45 (w/w) surfactant to oil.

3. The composition as defined in claim 1, wherein the oil is a mono-unsaturated triacylglycerol oil.

4. The composition of claim 3, wherein the oil is an oleic acid-containing oil.

5. The composition of claim 1, wherein the oil is selected from the group consisting of high-oleic sunflower, high-oleic & high-stearic sunflower oil, high-oleic soybean, high-oleic canola, high-oleic safflower oil, sunflower oil, safflower oil, soybean oil, algal oil, microbial oil, canola oil, avocado oil, olive oil, medium and short-chain saturated triglyceride oils and mixtures thereof.

6. The composition as defined in claim 1, comprising ethylcellulose having a viscosity selected from the group consisting of 4 cp, 10 cp, 22 cp, 45 cp, 100 cp and 300 cp, or comprising a mixture of ethylcellulose having viscosities selected from the group consisting of 4 cp, 10 cp, 22 cp, 45 cp 100 cp and 300 cp.

7. The composition as defined in claim 1, wherein the surfactant comprises at least one of myristoleate, palmitoleate, oleate and gadoleate.

8. The composition as defined in claim 1 wherein the surfactant is selected from the group consisting of polyoxyethylene sorbitan monooleate (Tween 80), sorbitan monooleate (SMO or Span 80), glyceryl monooleate (GMO), glyceryl dioleate, polyglyceryl ester of oleic acid (PGO), polyglyceryl polyoleate (PGPO) and polyglyceryl polyricinoleate (PGPR).

9. The composition as defined in claim 8, wherein the surfactant is GMO.

10. The composition of claim 1, wherein the ethylcellulose concentration is about 5-10%.

11. The composition of claim 1, having an equilibrium viscosity of less than about 100 Pa s.

12. The composition of claim 11, having an equilibrium viscosity of about 2-50 Pa s.

13. The composition of claim 1, wherein the degree of ethoxylation of ethylcellulose is about 25% to about 75%.

14. A method of preparing a thixotropic composition comprising:
   a) combining ethylcellulose in an amount ranging from 1-15% by weight with a triacylglycerol oil and a nonionic surfactant, wherein the combination of the triacylglycerol oil and surfactant is in the range of about 85-99 wt % and wherein the ratio of surfactant to oil is in the range of about 40:60 to 60:40 (w/w) to form a mixture;
   b) heating the mixture until the ethylcellulose is solubilized; and
   c) allowing the mixture to cool to form a thixotropic composition.

15. The method of claim 14, wherein the surfactant to oil ratio is in the range of about 45:55 to 55:45 (w/w) surfactant to oil.

16. The method as defined in claim 14, wherein the oil is a mono-unsaturated triacylglycerol oil.

17. The method of claim 16, wherein the oil is an oleic acid-containing oil.

18. The method of claim 16, wherein the oil is selected from the group consisting of high-oleic sunflower, high-oleic & high-stearic sunflower oil, high-oleic soybean, high-oleic canola, high-oleic safflower oil, canola oil, avocado oil, olive oil, sunflower oil, safflower oil, soybean oil, algal oil, microbial oil, medium and short-chain saturated triglyceride oils and mixtures thereof.

19. The method as defined in claim 14, wherein the surfactant is selected from the group consisting of polyoxyethylene sorbitan monooleate (Tween 80), sorbitan monooleate (SMO or Span 80), glyceryl monooleate (GMO), glyceryl dioleate (DGO), polyglyceryl ester of oleic acid (PGO), polyglyceryl polyoleate (PGPO) and polyglyceryl polyricinoleate (PGPR).

20. The method of claim 14, wherein the surfactant comprises at least one of myristoleate, palmitoleate, oleate and gadoleate.

* * * * *